United States Patent [19]
Nagata et al.

[11] Patent Number: 6,104,484
[45] Date of Patent: Aug. 15, 2000

[54] MEASURING CHIP FOR OPTICAL ANALYZER

[75] Inventors: Ryohei Nagata; Hiroyuki Nakamura, both of Shinjuku-ku, Japan

[73] Assignee: Dai Nippon Printing Co., Ltd., Japan

[21] Appl. No.: 09/044,847

[22] Filed: Mar. 20, 1998

[30] Foreign Application Priority Data

| Mar. 26, 1997 | [JP] | Japan | ................................... 9-073313 |
| May 21, 1997 | [JP] | Japan | ................................... 9-131315 |
| Jul. 4, 1997 | [JP] | Japan | ................................... 9-179587 |

[51] Int. Cl.$^7$ ............................. G01N 1/10; G01N 21/00
[52] U.S. Cl. ............................................. 356/246; 422/58
[58] Field of Search .............................. 356/36, 244, 246, 356/128, 132, 445; 250/306, 307; 422/82.11, 82.09, 82.05, 102, 101, 68, 58; 435/288, 301, 311, 817, 7

[56] References Cited

U.S. PATENT DOCUMENTS

| 4,889,427 | 12/1989 | Van Veen et al. | ....................... 356/445 |
| 4,978,503 | 12/1990 | Shanks et al. | ............................. 422/58 |
| 4,997,278 | 3/1991 | Finlan et al. | ............................. 356/128 |
| 5,327,225 | 7/1994 | Bender et al. | ........................... 356/445 |
| 5,374,563 | 12/1994 | Manie | ..................................... 436/165 |
| 5,397,537 | 3/1995 | Kanda et al. | ............................. 422/56 |
| 5,822,073 | 10/1998 | Yee et al. | ................................. 356/445 |
| 5,869,272 | 2/1999 | Bogart et al. | ........................... 435/7.32 |

FOREIGN PATENT DOCUMENTS

| E 92 186 | 2/1994 | Austria . |
| 44 24 336 A1 | 1/1996 | Germany . |

*Primary Examiner*—Frank G. Font
*Assistant Examiner*—Michael P. Stafira
*Attorney, Agent, or Firm*—Parkhurst & Wendel, L.L.P

[57] ABSTRACT

A measuring chip for an optical analyzer includes a translucent or transparent substrate 1, and a sample solution chamber S formed on a sulface of the translucent or transparent substrate 1. The sample solution chamber S has an inlet $S_1$ for introducing a sample solution to be analyzed, and an outlet $S_2$ for discharging the analyzed sample solution. The sample solution chamber S is formed so as to be filled with the sample solution between the inlet $S_1$ and the vicinity of the outlet $S_2$ by the capillary phenomenon. On the translucent or transparent substrate 1, an analyzing region 10 is formed by stacking a metal thin film 2 and an immobilizing film 3 for immobilizing a physiologically active substance 4. On the analyzing region 10, the sample solution chamber S is formed to obtain a measuring chip for an optical analyzer particularly utilizing the surface plasmon resonance (SPR). Thus. it, is possible to obtain a measuring chip for an optical analyzer, which can be easily handled and which can carry out an analysis using a small quantity of sample solution.

31 Claims, 11 Drawing Sheets

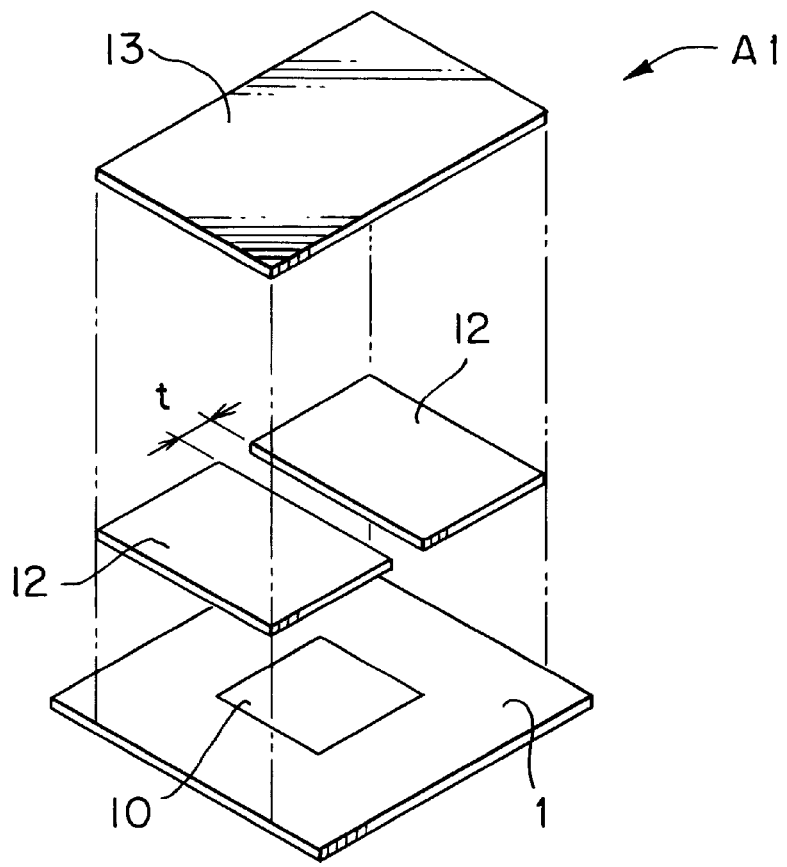
F I G. 2 (a)
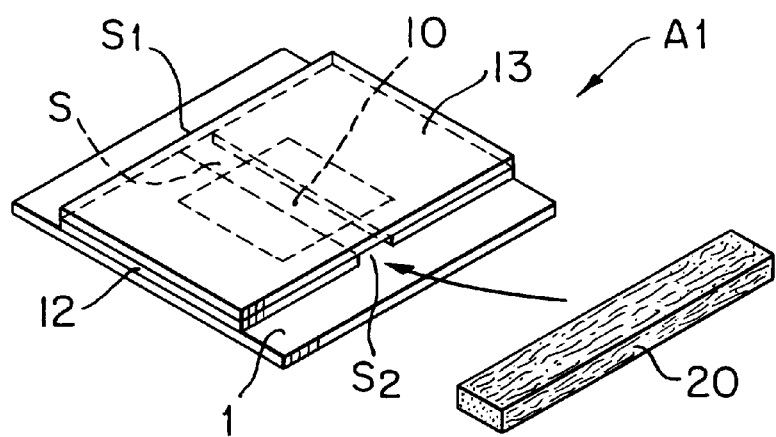
F I G. 2 (b)

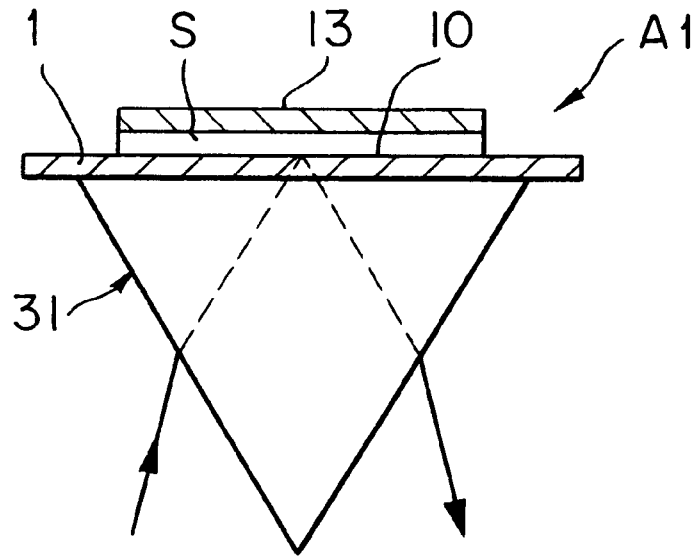
F I G. 4
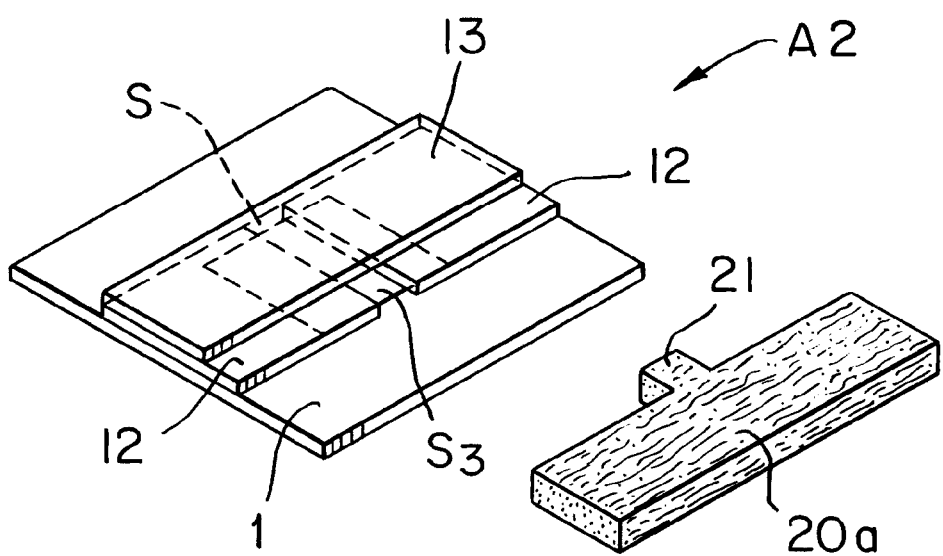
F I G. 5

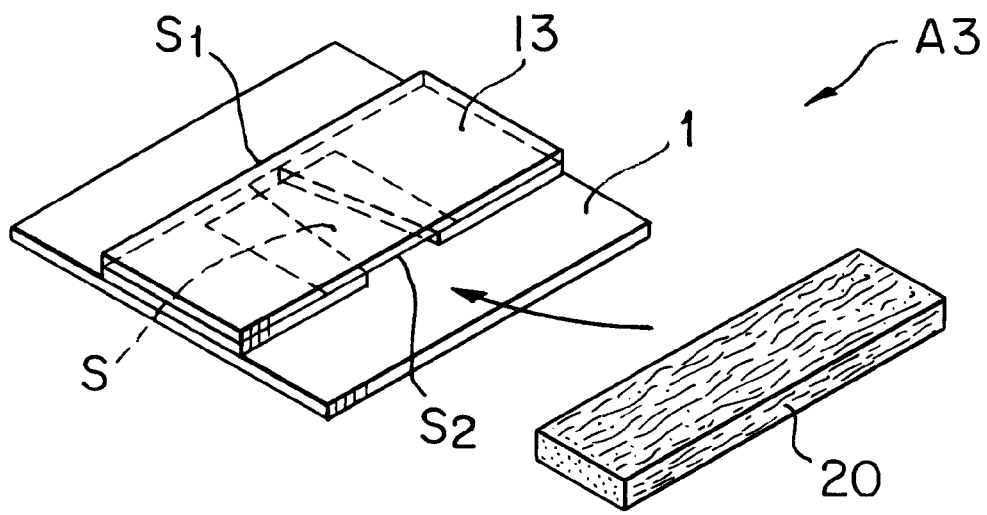
F I G. 6
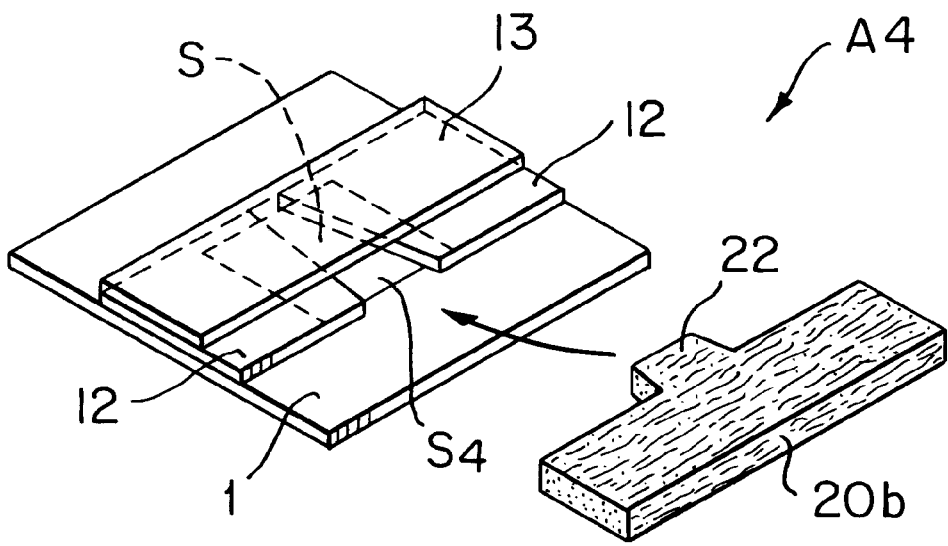
F I G. 7

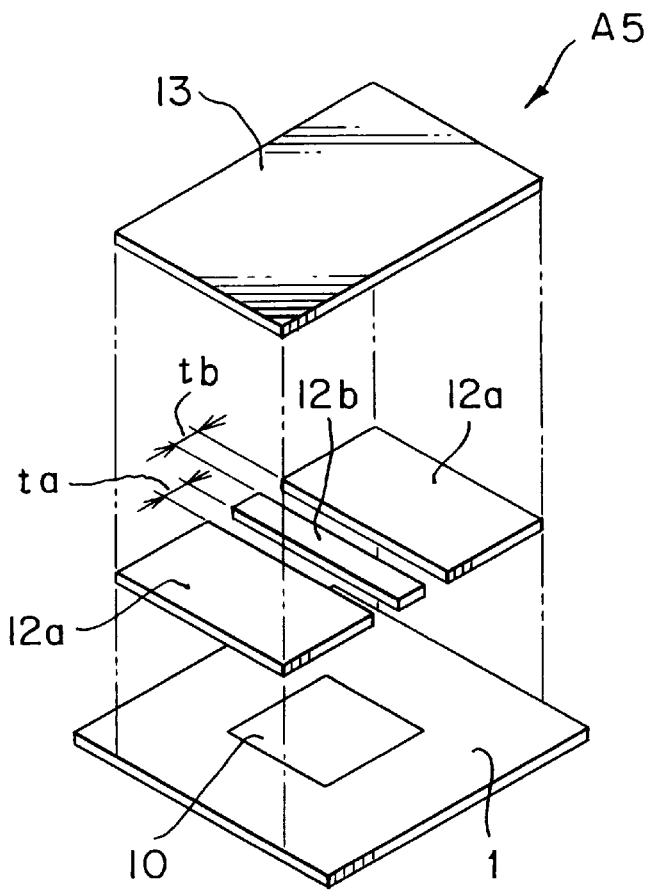
F I G. 9(a)
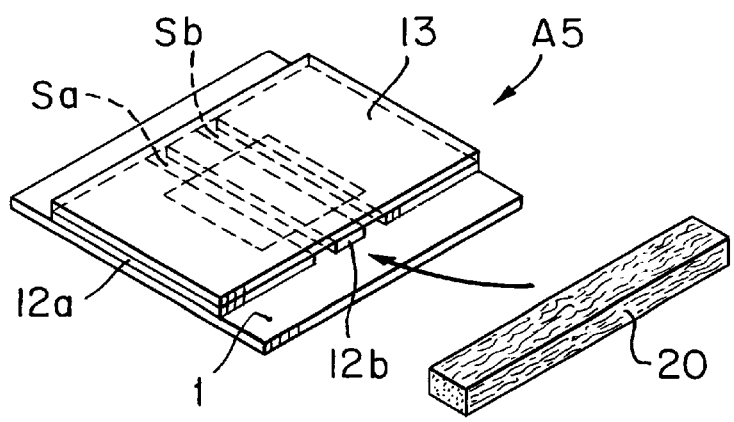
F I G. 9(b)

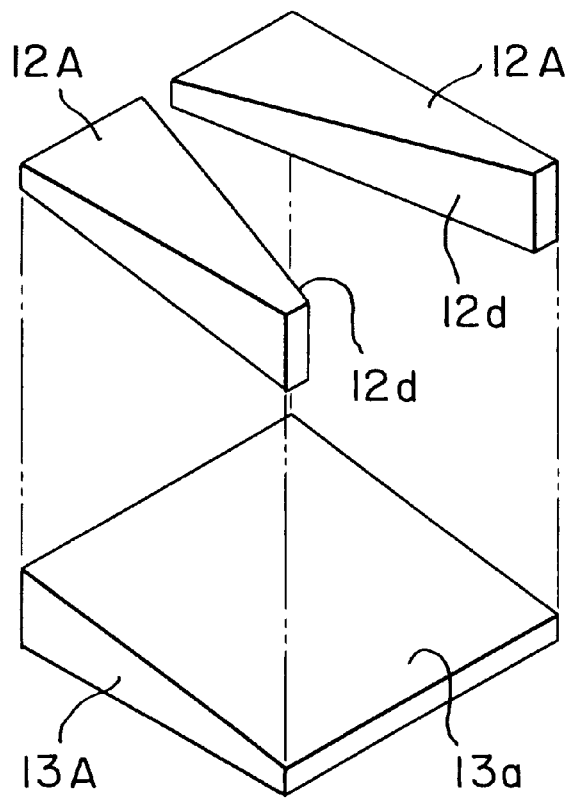
F I G. 16 (a)
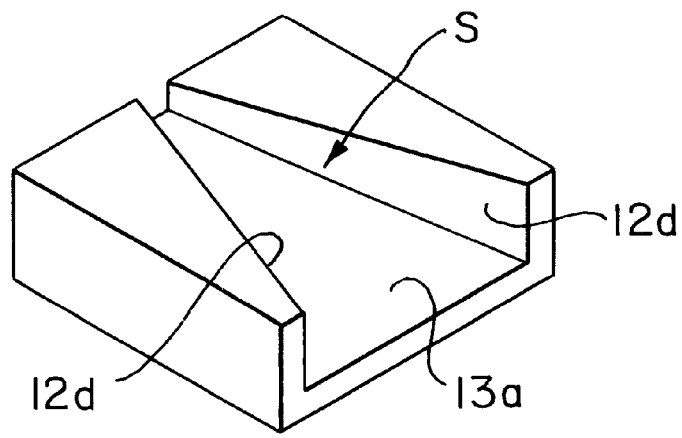
F I G. 16 (b)

MEASURING CHIP FOR OPTICAL ANALYZER

BACKGROUND OF THE INVENTION

1. Field of The Invention

The present invention relates generally to a measuring chip for an optical analyzer. More specifically, the invention relates to a measuring chip for an optical analyzer, which is effectively used to optically analyze a sample by irradiating a sample solution, which is introduced onto a translucent or transparent substrate, with light.

2. Description of the Prior Art

Analytic operation for irradiating a sample solution arranged on a translucent or transparent substrate with light to analyze a sample on the basis of variables, such as the refractive index and absorptivity of reflected light and transmission light, is often carried out. As an example of an examination method utilizing an immune reaction in a clinical examination or the like, there is an optical analyzing method capable of detecting a change of a physiologically active substance with high sensitivity, e.g., an optical analyzing method utilizing the surface plasmon resonance (SPR).

In the case of the optical analyzing method utilizing the surface plasmon resonance, a typical measuring chip for use in an optical analyzer comprises a translucent or transparent substrate, a metal thin film formed thereon, and an immobilizing film, which is formed thereon and to which a physiologically active substance suitable for an object to be analyzed is immobilized. The measuring chip having such a construction is set on a prism of the optical analyzer so that the translucent or transparent substrate faces the prism. A sample solution is continuously fed onto the surface of the immobilizing film by means of a supplying pump, or the liquid surface in a cell for containing a sample solution therein is arranged so as to contact the immobilizing film, so that the physiologically active substance interacts with the object to be analyzed (see, e.g., Japanese Patent Publication No. 5-2181, Japanese Patent Laid-Open No. 63-75542).

As described above, in most conventional optical analyzers, the supplying pump or the sample solution containing cell is used to supply the sample solution to the measuring chip. Therefore, the conventional optical analyzers are large-scale and complicated. In addition, although the quantity of a sample solution required for a single measuring chip for an optical analyzer to measure a sample is very small, it is necessary to prepare a large quantity of sample solution for an analysis. For that reason, the development of a small analyzer having excellent portability has been far behind.

In the case of the optical analyzing method utilizing the surface plasmon resonance, the incident light entering the reverse surface of the translucent or transparent substrate and the reflected light from the metal thin film are optically analyzed to obtain necessary information, and it is sufficient for a very small quantity of sample solution to exist on the metal thin film on the surface of the translucent or transparent substrate. However, in fact, it is required to prepare a large sample volume, so that it takes a lot of time and money to prepare the sample.

SUMMARY OF THE INVENTION

It is therefore an object of the present invention to eliminate the aforementioned problems and to provide a measuring chip for an optical analyzer, which does not require any complicated supplying means, such as a supplying pump, for supplying a sample solution and which can sufficiently achieve the analysis of the sample by supplying only a very small quantity of sample solution to the measuring chip, so that the preliminary work can be completed in a short time and at low costs.

In order to accomplish the aforementioned and other objects, the inventors diligently studied and found that a sufficient quantity of sample solution to achieve the analysis of the sample was introduced into a sample solution chamber on a substrate by utilizing the capillary phenomenon, so that the inventors made the present invention.

According to one aspect of the present invention a measuring chip for an optical analyzer comprises a translucent or transparent substrate, and a sample solution chamber, which has an inlet and an outlet and which is formed on a surface of the translucent or transparent substrate so that the interior of the sample solution chamber from the inlet to the vicinity of the outlet is capable of being filled with a sample solution by the capillary phenomenon.

Throughout the specification, the term "optical analyzer" means a system or apparatus capable of optically analyzing an object to be analyzed. For example, the optical analyzers include ultraviolet, infrared, visible radiation, fluorescence and Raman spectrometers, i addition to the optical analyzer utilizing the surface plasmon resonance. In addition, the term "measuring chip" for an optical analyzer generally means a member capable of carrying an object to be analyzed, in and out of a light irradiation region of the optical analyzer.

The sample solution chamber may be arranged directly on the translucent or transparent substrate. In the case of the measuring chip for use in an optical analyzer for carrying out various measurements by utilizing an immune reaction in a clinical examination, an immobilizing film for immobilizing a physiologically active substance to the surface of the translucent or transparent substrate may be provided, and the sample solution chamber may be formed thereon. It is not required to provide the immobilizing film on the whole surface of the translucent or transparent substrate if the immobilizing film is formed at least in a region irradiated with light for the analysis. At least a part of the immobilizing film is arranged so as to face the sample solution chamber so that the interior of the sample solution chamber between the inlet and the vicinity of the outlet may be filled with the sample solution by the capillary phenomenon.

As described above, in the case of the measuring chip for use in the optical analyzer utilizing the surface plasmon resonance, a metal thin film may be provided on at least the surface of the translucent or transparent substrate, and the immobilizing film for immobilizing the physiologically active substance to the surface of the metal thin film may be provided.

When the measuring chip for the optical analyzer according to the present invention is used, a sample solution to be analyzed, which is preferably contained in a small portable container, such as a pipette and a syringe, may be caused to drop into the vicinity of the inlet of the sample solution chamber formed on the translucent or transparent substrate. The chopped sample solution may enter the sample solution chamber to approach the outlet by the capillary phenomenon so that the sample solution chamber is filled with the sample solution. In this state, the measuring chip may be set in the optical analyzer to carry out a required optical analyzing operation. After the operation, the measuring chip may be removed from the optical analyzer, and the sample solution may be discharged from the sample solution chamber by producing a pressure difference or the like.

A sample solution chamber or two sample solution chambers or more may be formed on the translucent or transparent substrate. In the latter, a plurality of sample solutions can be simultaneously analyzed, and one of the sample solution chambers can be used as a sample solution chamber for reference, so that it can be easy to obtain more accurate measurement results. Alternatively, at least one sample solution chamber may have both of a reference region and a sample region. Also in this case, the same advantages can be obtained. In this case, the respective sample solution chambers or the respective regions are preferably irradiated with light beams being in the same conditions by dividing a light beam emitted from the same light source into a plurality of systems by means of a beam splitter or the like. When the optical analyzer has a plurality of light sources, the respective sample solution chambers or the respective regions are preferably irradiated with light beams, which are processed so as to be in the same conditions in the respective systems. When a single beam is used, the measuring chip may be caused to slide so that the respective sample solution chambers or the respective regions are irradiated with light.

In a preferred embodiment of the present invention, the measuring chip for the optical analyzer further comprises an absorbing pad for absorbing and discharging the sample solution. In this case, the sample solution can be easily discharged by bringing the absorbing pad into contact with the outlet of the sample solution chamber. Alternatively, a plurality of absorbing pads having different rates of absorption may be prepared to be selectively used in accordance with the environment for measurement or the like. In a preferred embodiment of the present invention, the side walls of the sample solution chamber are inclined with respect to the flowing direction of the sample solution, or the upper and lower surfaces of the sample solution chamber are inclined with respect to the reference level for measurement. Both may be adopted. Thus, the cross-sectional area of the sample solution chamber on the side of the outlet may be greater or smaller than that on the side of the inlet. In the former, there is an advantage in that the rate of the sample solution discharged by the absorbing pad can be increased. In the latter, there is an advantage in that all the sample solution can be surely discharged from the sample solution chamber without running out of the sample solution during the absorption of the sample solution.

BRIEF DESCRIPTION OF THE DRAWINGS

The present invention will be understood more fully from the detailed description given herebelow and from the accompanying drawings of the preferred embodiments of the invention. However, the drawings are not intended to imply limitation of the invention to a specific embodiment, but are for explanation and understanding only.

In the drawings:

FIG. 2(a) is an exploded perspective view of the first preferred embodiment of a measuring chip for an optical analyzer according to the present invention, and FIG. 2(b) is a perspective view of the measuring chip of FIG. 2(a) after being assembled;

FIG. 4 is a schematic view illustrating the state that the measuring chip of FIGS. 2(a) and 2(b) is set on an optical analyzer;

FIG. 5 is a perspective view of the second preferred embodiment of a measuring chip for an optical analyzer according to the present invention;

FIG. 6 is a perspective view of the third preferred embodiment of a measuring chip for an optical analyzer according to the present invention;

FIG. 7 is a perspective view of the fourth preferred embodiment of a measuring chip for an optical analyzer according to the present invention;

FIGS. 9(a) and 9(b) are perspective views of the fifth preferred embodiment of a measuring chip for an optical analyzer according to the present invention;

FIGS. 16(a) and 16(b) are perspective views of embodiments of a sample solution chamber of a measuring chip for an optical analyzer according to the present invention.

DESCRIPTION OF THE PREFERRED EMBODIMENTS

Referring now to the accompanying drawings, the preferred embodiments of a measuring chip for an optical analyzer according to the present invention will be described in detail below. Furthermore, while a measuring chip suitable for an immune center, which serves as an optical analyzer and which utilizes the surface plasmon resonance, will be described as an example, a measuring chip for an optical analyzer according to the present invention should not be limited thereto, but it may be a measuring chip for use in other optical analyzers.

The surface plasmon resonance phenomenon is caused by the fact that the intensity of a monochromatic light reflected on the boundary between an optically transparent material, such as glass, and a metal thin film layer depends on the refractive index of a sample on the outgoing radiation side of the metal. Therefore, the sample can be analyzed by measuring the intensity of the reflected monochromatic light. The measuring chip used for the optical analyzer basically comprises a translucent or transparent substrate, a metal thin film formed on a surface of the substrate, and an immobilizing film formed on the metal thin film for immobilizing a physiologically active substance.

Figure 1:
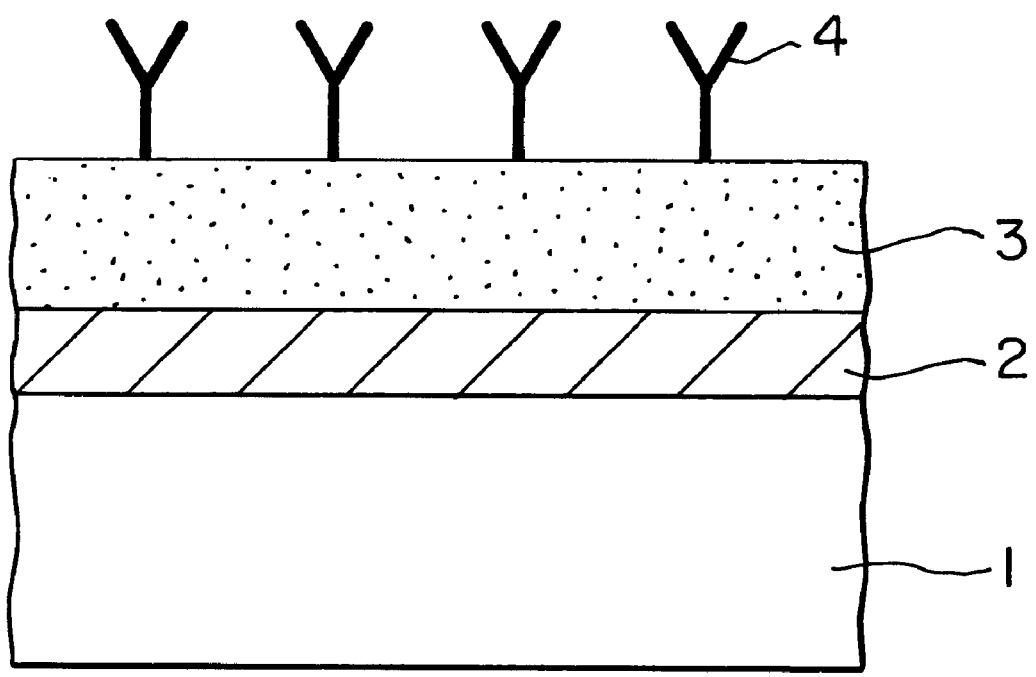
FIG. 1 is a schematic sectional view illustrating a principal part of a measuring chip suitable for an optical analyzer utilizing the surface plasmon resonance.

FIG. 1 is a schematic sectional view illustrating a principal part of a measuring chip suitable for an optical analyzer utilizing the surface plasmon resonance. As shown in FIG. 1, the measuring chip comprises a translucent or transparent substrate 1, a metal thin film 2 formed thereon, and an immobilizing film 3 formed thereon for immobilizing a physiologically active substance 4. The translucent or transparent substrate 1 is generally made of glass or a transparent material to laser radiation, and has a thickness of about 0.1 to 5 mm.

The metal thin film 2 may be made of a material capable of causing the surface plasmon resonance, e.g., a material selected from the group consisting of gold, silver, platinum, copper, aluminum and the combinations thereof. In view of the adhesive property to the translucent or transparent substrate 1, an intercalated layer of chromium or the like may be provided between the translucent or transparent substrate 1 and the layer of gold, silver or the like. The thickness of the metal thin film 2 is preferably in the range of from 100 Å to 2000 Å, and more preferably in the range of from about 100 Å to about 500 Å.

The physiologically active substance 4 may be a substance capable of interacting with an object to be analyzed (e.g., antigen), and may be selected from the group consisting of immuno proteins, enzymes, microorganisms and bacteria. For example, the immuno protein may be an antibody, the antigen of which is an object to be analyzed. The antibody may be selected from various immunoglobuhins, such as IgG, IgM, IgA, IgE and IgD. Specifically, when the object to be analyzed is human serum albumin, the antibody may be human serum albumin antibody. When the antigen is selected from the group consisting of pesticides, insecticides, methicillin tolerant Staphylococcus aureus, antibiotics, narcotic, cocaine, heroin and crack, the antibody may be atrazine antibody, antikanamycin antibody or antimethamphetamine antibody.

The enzymes may include any enzymes, that have activity against the object to be analyzed or a substance metabolized from the object to be analyzed. For example, the enzymes may include oxidoreductases, hydrolases, isomerases, eliminating enzymes and synthetic enzymes. Specifically, when the object to be analyzed is glucose, the enzyme may be glucose oxidase, and when the object to be analyzed is cholesterol, the enzyme may be cholesterol oxidase. When the object to be analyzed is selected from the group consisting of pesticides, insecticides, methicillin tolerant Staphylococcus aureus, antibiotics, narcotic, cocaine, heroin and crack, the enzyme may be selected from any enzymes, that are capable of specifically reacting with a substance metabolized from the object to be analyzed. e.g. acetylcholine esterase, catecholamine esterase, noradrenaline esterase and dopamine esterase.

The microorganisms and bacteria may include various microorganisms and bacteria, such as *Escherichia coli*. The physiologically active substance 4 may be DNA base chains, and complementary base chains can specifically bonded.

The immobilizing film 3 for immobilizing the physiologically active substance 4 may be a layer of a porous material capable of supporting or immobilizing the physiologically active substance 4. The porous material may be selected from woven fabric, knit fabric and non woven fabric, which are made of synthetic fiber, natural fiber or inorganic fiber, and inorganic and organic porous materials (see Japanese Patent Laid-Open No. 3-164195). Alternatively, the immobilizing film 3 may be a thin film of a material having a specific functional group based on a chemical or biochemical reaction.

A method for immobilizing the physiologically active substance 4 to the immobilizing film 3 may be any one of conventional methods. For example, the physiologically active substance 4 can be immobilized by a method for contacting a predetermined quantity of physiologically active substance 4 to the immobilizing film 3 for a predetermined period of time, or by the impregnation, microdispensing, gravure or screen process printing.

In Japanese Patent Application No. 8-323098, the inventors have disclosed a film having both functions of the metal thin film 2 and the immobilizing film 3 by arranging metal colloidal particles, to the surface of which functional groups are introduced, on a translucent or transparent substance in the form of closest packing. The functional-group introduced metal colloidal particle means a metal colloidal particle, to the surface of which a functional group is introduced and which has a colloid size ranging from 10 through 1000 nm. The metal of the metal colloidal particle may be selected from any metals capable of performing an optical analysis, and usually selected from the group consisting of gold, platinum, silver, aluminum and the combinations thereof If such functional-group introduced metal colloidal particles are used, the physiologically active substance bonded to the functional group is immobilized close to the metal colloidal particles, so that there is an advantage in that the measuring sensitivity can be considerably improved in comparison with the use of an immobilizing film of a metal thin film and an organic thin film. Also in a measuring chip for an optical analyzer according to the present invention, such a layer may be used as a layer arranged on the translucent or transparent substrate 1.

The functional group may be selected from any functional groups capable of immobilizing a desired physiologically active substance to metal colloidal particles. The functional group is preferably an amino group or a mercapto group. The amino group is capable of forming a strong bond particularly to a physiologically active substance containing aspartic acid, glutamic acid or the like in the primary structure thereof, or to a C-terminal (a carboxyl terminal) of an organism related substance, such as an antibody or a nucleic acid. The mercapto group is capable of forming a strong bond particularly to a physiologically active substance containing cysteine, methionine or the like in the primary structure thereof. At these points, amino and mercapto groups are desired.

Furthermore, the term "the form of closest packing" means the state that distal functional groups occupy the outermost layer and the functional groups are densely packed so that other molecules can not be inserted between the adjacent metal colloidal particles. Thus, if the functional-group introduced metal colloidal particles are arranged on the substrate in the form of closest packing, the physiologically active substance can be densely and uniformly immobilized, so that the measuring sensitivity can be improved. The detailed descriptions thereof are described in Japanese Patent Application No. 8-323098, which is assigned to the present Assignee and incorporated herein by reference.

Referring to FIGS. 2(a) and 2(b), the detailed construction of the first preferred embodiment of a measuring chip for an optical analyzer utilizing the surface plasmon resonance, according to the present invention, will be described below.

FIG. 2(a) is an exploded perspective view of the first preferred embodiment of a measuring chip for an optical analyzer according to the present invention, and FIG. 2(b) is a perspective view of the measuring chip of FIG. 2(a) after being assembled. In this preferred embodiment, a measuring chip A1 of an optical analyzer includes a translucent or transparent substrate 1, which is a rectangular glass plate having a length of about 18 mm and a thickness of about 0.1 to 0.2 mm. The substrate 1 may be made of a resin, such as a non-oriented polyethylene terephthalate or a non-oriented polycarbonate, which has translucency or transparency, no anisotropy to polarization, and excellent properties for workability.

At the central portion of one surface of the translucent or transparent substrate 1, an analyzing region 10 is formed by staking a metal thin film 2 and an immobilizing film 3. On the one surface of the translucent, or transparent substrate 1, on which the analyzing region 10 is formed, a pair of side plates 12, each of which is formed of a Teflon sheet having a width of 12 mm and a thickness of 0.2 mm, are stacked so that all or a part, of the surface of the analyzing region 10 is exposed (a part thereof is exposed in the shown embodiment). The distance t between the side plates 12 is 2 mm. On the upper surfaces of the side plates 12, a top board 13 of a Teflon sheet having a width of about 12 mm and a thickness of about 0.1 to 0.2 mm is stacked. Thus, a space S (a sample solution chamber) having a width of 2 mm×a length of 12 mm×a height of 0.2 mm is formed on the upper side of the translucent or transparent substrate 1, so that the volume of the space S is 4.8 cc.

The materials of the side places 12 and the top board 13 should not be limited to the Teflon sheet, but the materials may be industrial plastics or glass. As will be described later, the size of the space S may be optionally selected if the sample solution can enter from an inlet $S_1$ to reach the vicinity of an outlet $S_2$ by the capillary phenomenon, and may be determined by calculation or experiment in accordance with the kind of the sample solution and the materials of the translucent or transparent substrate 1, the wide plates 12 and the top board 13. In general, in the case of the capillary phenomenon, if the pipe wall is completely dipped into a liquid (a sample solution), a height H of a liquid column rising a capillary perpendicularly dipped into the liquid basically depends on the following formula:

$$\gamma=(\tfrac{1}{2}) \times r \rho \times g \times H$$

wherein r is a radius of the pipe, $\rho$ is a difference of density between a liquid and a gas contacting the liquid, and g is gravity. Using the above formula as a basic formula, the size of the space S may be set case by case.

In FIG. 2(b), reference number 20 denotes an absorbing pad, which is made of pulp, fabric, non woven fabric, absorbent cotton, filter paper or any one of high water-absorptive polymeric materials, such as polyacrylic acids, polyvinyl alcohols and polyethylene oxides. The provided absorbing pad 20 should not be limited to a single absorbing pad, but a plurality of absorbing pads having different materials so as to have different rates of absorption may be prepared to be selectively used.

Figure 3A:
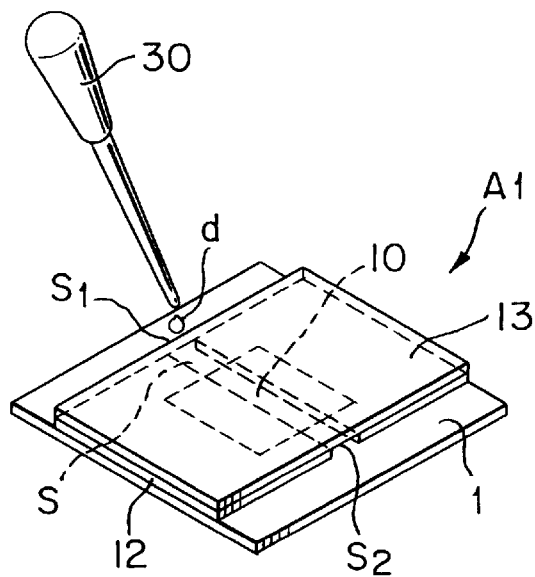
FIGS. 3(a) through 3(c) are perspective views explaining the method for using the measuring chip of FIGS. 2(a) and 2(b)
Figure 3B:
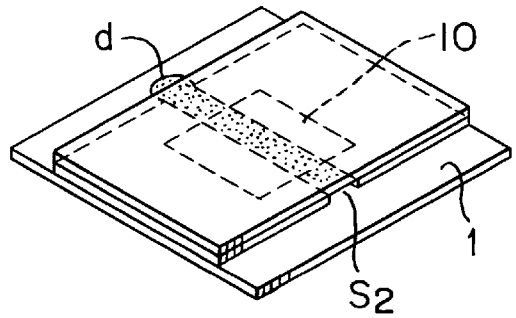
Figure 3C:
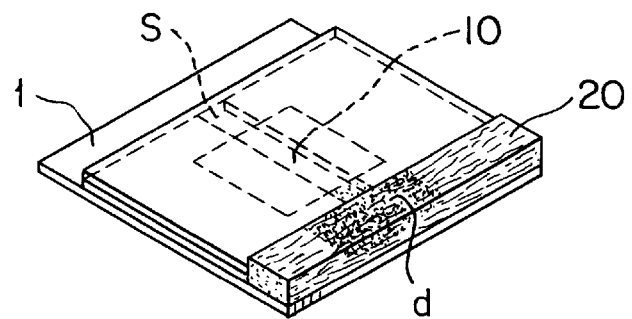

FIGS. 3(a) through 3(c) and FIG. 4 show a process for carrying out the optical analysis utilizing the surface plasmon resonance by means of the measuring chip A1 for the optical analyzer shown in FIGS. 2(a) and 2(b). As shown in FIG. 3(a), the operator causes the tip of a pipette 30 containing the sample solution to approach the inlet $S_1$ of the space S of the measuring chip A1, and causes a drop or a few drops of sample solution to fall into the inlet $S_1$. The dropped sample solution d enters the space S serving as the sample solution chamber to reach the outlet $S_2$ by the capillary phenomenon (see FIG. 3(b)). As a result, the surface of the analyzing region 10, at least, a part of which is exposed to the space S, is filled with the sample solution d, so that the physiologically active substance 4 immobilized to the immobilizing film 3 interacts with an object to be analyzed in the sample solution d.

Then, the measuring chip A1 is introduced into the optical analyzer and arranged so that the reverse surface thereof contacts a prism 31 of the analyzer as shown in FIG. 4. Then, the optical analysis utilizing the surface plasmon resonance is carried out by the conventional method. That is, a buffer or reference solution is caused to drop onto a measuring chip to measure a base line, and then, the buffer or reference solution is removed by means of an absorbing pad. Subsequently, a sample solution is caused to (drop onto the measuring chip to measure the surface plasmon resonance. When the absorbing pad 20 is used, the absorbing pad 20 is brought into contact with the outlet $S_2$ of the measuring chip A1 to absorb the sample solution d while the measuring chip A1 is arranged at the position in the optical analyzer or after the measuring chip A1 is removed from the optical analyzer (see FIG. 3(c)). When the absorbing pad 20 is used while the measuring chip A1 is mounted on the optical analyzer, the sample solution can be caused to drop while it is absorbed.

In another embodiment of the measuring chip, a reference region is formed by applying, e.g., glutaraldehyde, to a half region of the bottom of the sample solution chamber, and a sample region is formed by immobilizing an antibody to the other half region via glutaraldehyde. After the sample solution is dropped, the respective regions may be simultaneously irradiated with light by means of a measuring equipment having a double beam. In this case, the reference and sample can be simultaneously measured, so that the measurement can be efficiently carried out.

If a high-speed absorbing pad is used as the absorbing pad 20, a specimen, a rinsing solution and so forth can be exchanged for a short time, so that the high-speed absorbing pad can be effectively used as the absorbing pad 20 for calibration. On the other hand, if a low-speed absorbing pad is used as the absorbing pad 20, the sample solution can be dropped while it is absorbed by the absorbing pad 20, so that the same effects occur as those of an optical analysis in a so-called "flow system". Therefore, it is easy to efficiently carry out an optical analysis operation by using an absorbing pad 20 having different rates of absorption during calibration and during measurement.

As described above, if a measuring chip for an optical analyzer according to the present invention is used, a required optical analysis can be carried out by causing only a drop or a few drops of sample solution to fall every time the analysis is carried out, so that the preliminary operation for analysis can be simplified and the quantity of wasteful sample solution can be decreased. Thus, the optical analysis operation can be carried out, at low costs. In addition, since the sample solution is not easy to leak once entering the sample solution chamber S and since the operator's hand does not contact the sample solution, it is very quick and easy to carry the measuring chip in and out the analyzer, so that the analytical accuracy can be improved.

FIG. 5 shows the second preferred embodiment of a measuring chip for an optical analyzer according to the present invention. In this preferred embodiment, the width of a top board 13 is less than those of side plates 12. At this point, a measuring chip A2 in this preferred embodiment is different from the measuring chip A1. In this case, the outlet of a sample solution chamber (space) S has a portion $S_3$, which is open upwards, so that the discharging operation of the sample solution can be easily carried out. In the case of the measuring chip A2 in this preferred embodiment, a projecting portion 21 capable of entering the portion $S_3$ is provided on a side of an absorbing pad 20a, so that a waste solution can be easily and quickly discharged.

FIG. 6 shows the third preferred embodiment of a measuring chip for an optical analyzer according to the present invention. In this preferred embodiment, the light and left side walls of a sample solution chamber (space) S are inclined with respect to the flowing direction of the sample solution so that the cross-sectional area of the outlet $S_2$ of the sample solution chamber S is greater than that of the inlet $S_1$ thereof. At this point, a measuring chip A3 in this preferred embodiment is different from the measuring chip A1. In this case, there is an advantage in that the rate of discharge of the sample solution can be increased to quickly carry out the measurement.

FIG. 7 shows the fourth preferred embodiment of a measuring chip for an optical analyzer according to the present invention. In this preferred embodiment, the width of a top board 13 is less than those of side plates 12. At this point, a measuring chip A4 in this preferred embodiment is different, from the measuring chip A3. Therefore, similar to the measuring chip A2, the outlet of a sample solution chamber (space) S has a portion $S_4$, which is open upwards, so that the discharging operation of the sample solution can be easily carried out. Also in this case, a projecting portion 22 (preferably a trapezoid projecting portion 22 as shown in FIG. 7) capable of entering the portion $S_4$ is provided on a side of an absorbing pad 20b.

Figure 8:
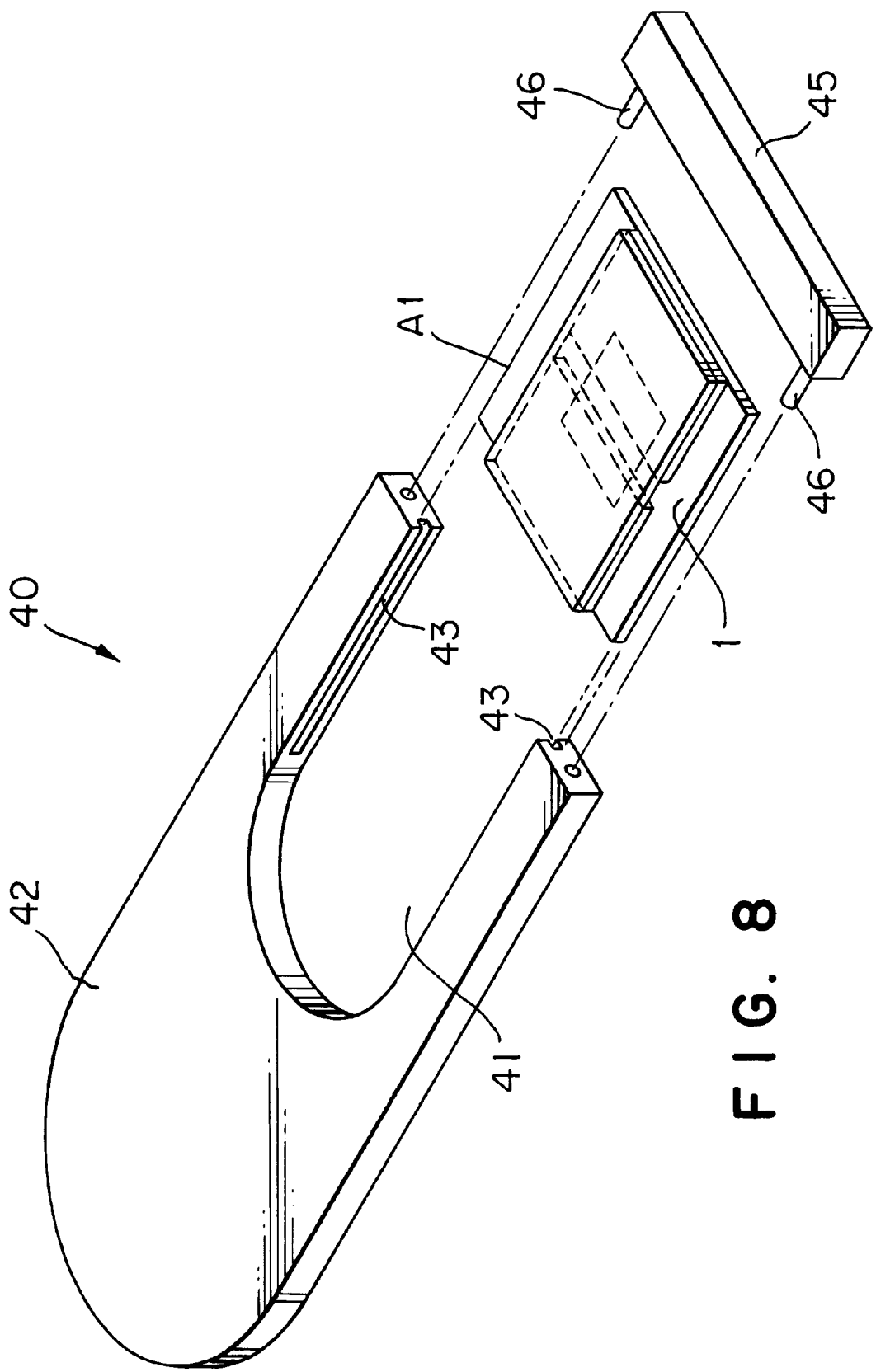
FIG. 8 is a perspective view of a preferred embodiment of a measuring chip having a carrying holder for an optical analyzer according to the present invention.

FIG. 8 shows a carrying holder 40 for allowing the measuring chip to be easily set in and ejected from the optical analyzer. The carrying holder 40 is made of a general plastic, such as a polypropylene or a polyvinyl chloride. The carrying holder 40 comprises a measuring-chip engaging portion 41 provided on one side, and a holder portion (handle) 42 provided on the other side and held by the operator's hand for carrying. The measuring-chip engaging portion 41 has a pair of grooves 43 on both sides for receiving the peripheral portion of the translucent or transparent substrate 1 of, e.g., the measuring chip A1, so that the measuring chip A1 engages the carrying holder 40. Reference number 45 denotes a fastening member used if necessary. The fastening member 45 has a pair of insert pins 46, which is inserted into holes formed in the measuring chip engaging portion 41 for preventing the measuring chip from moving and being disengaged. The whole holder including the measuring chip may be disposable. Since the shown measuring chip A1 is only an example, other measuring chips (e.g., the measuring chips A2 through A4 shown in FIGS. 5 through 7 or measuring chips A5 and AG shown in FIG. 9 through 12, which will be described later) may be optionally used.

FIGS. 9(a) and 9(b) show the fifth preferred embodiment of a measuring chip for an optical analyzer according to the present invention. In this preferred embodiment, two sample solution chambers (spaces) Sa, Sb are formed in parallel. At this point, a measuring chip A5 in this preferred embodiment is different from the measuring chip A1. FIG. 9(a) is an exploded perspective view of the measuring chip A5, and FIG. 9(b) is a perspective view of the measuring chip A5 after being assembled. As shown in FIGS. 9(a) and 9(b), a translucent or transparent substrate 1, an analyzing region 10 formed by stacking a metal thin film and an immobilizing film, and a top board 13 are the same as those of the measuring chip A1. On the surface of the substrate 1, on which the analyzing region 10 is formed, a pair of right and left side plates 12a are formed at regular intervals. Between the side plates 12a, a center plate 12b is stacked on the substrate 1 so as to be apart from the side plates 12a by distances ta and tb, respectively. The top board 13 is stacked thereon similar to the measuring chip A1. The materials and thickness of the side plates 12a and the center plate 12b may be the same as those of the measuring chip A1.

With this construction, as shown in FIG. 9(b), the measuring chip A5 has two sample solution chambers Sa, Sb arranged substantially in parallel. If the distances ta and tb are equal to each other, the volumes of the sample solution chambers Sa, Sb are also equal to each other. The sizes of the sample solution chambers Sa, Sb may be optionally selected if the sample solution can enter the inlet to reach the vicinity of the outlet by the capillary phenomenon. The sizes of the sample solution chambers Sa, Sb may be the same as or different from those of the sample solution chamber S of the measuring chip A1. Preferably, the shape and size of the sample solution chamber Sa is the same as those of the sample solution chamber Sb.

A method for using the measuring chip A1 is basically the same as that described referring to FIGS. 2 through 8. That is, the measuring chip A5 filled with the sample solution d is arranged so that the reverse surface of the measuring chip A5 contacts the prism 31a. Then, as shown in FIG. 10, the two sample solution chambers Sa, Sb are irradiated with separate light beams B1, B2 from the optical analyzer, so that the optical analysis e.g., utilizing the surface plasmon resonance, can be carried out simultaneously with respect to the sample solution d filled in the two sample solution chambers Sa, Sb.

The liquid filled in the two sample solution chambers Sa, Sb can be optionally selected. Two different kinds of sample solutions may be simultaneously analyzed. Alternatively, one sample solution chamber may be filled with a reference solution to be used as a reference sample solution chamber. In either case, a compensation treatment required for the irradiation light beams is previously carried out so that the measurement conditions are the same. If the light emitted from the same light source is divided into two systems by means of a beam splitter, the compensation treatment can be substantially omitted.

In the preferred embodiment shown in FIGS. 9(a) and 9(b), while the sample solution chamber has the inlet and outlet of the same cross-sectional areas and the top board 13 covering the whole upper surface of the sample solution chamber, the present invention should not be limited thereto. For example, each of two sample solution chambers may be the same as the sample solution chamber having the inlet and outlet of different cross-sectional areas as shown in FIG. 6, or the sample solution chamber having the top board 13, which does not cover a part of the upper surface of the sample solution chamber, as shown in FIG. 5. These sample solution chambers may be combined. Alternatively, three or more sample solution chambers may be used. In this case, the number of the light beams may be the same as that of the sample solution chambers. If the number of the light beams is less than that of the sample solution chambers, the measuring chip A5 may slide on the prism to carry out a plurality of analyzing operations.

Figure 10:
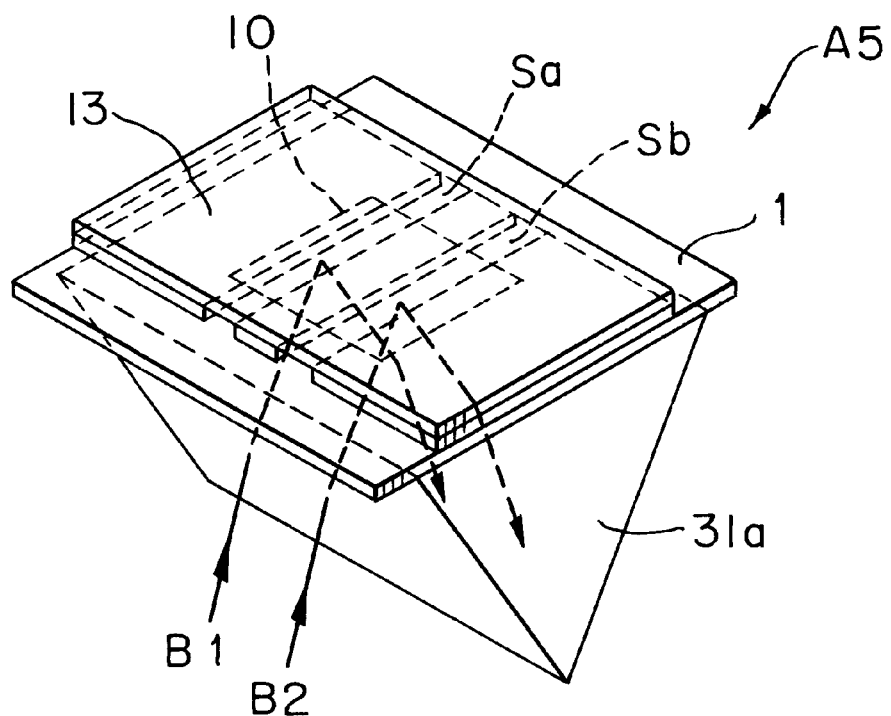
FIG. 10 is a schematic view illustrating the state that the measuring chip of FIGS. 9(a) and 9b) is set on an optical analyzer.

If a plurality of sample solution chambers are formed on a single measuring chip, there are also advantages in that it is possible to decrease the time required to measure plural numbers of sample, and it is possible to decrease mechanical errors caused when the measuring chip is mounted as shown in FIG. 10.

Figure 11:
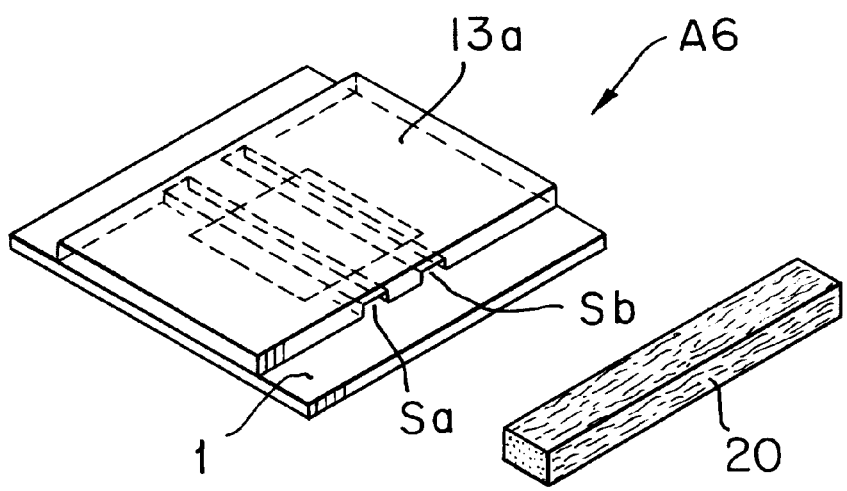
FIG. 11 is a perspective view of the sixth preferred embodiment of a measuring chip for an optical analyzer according to the present invention.
Figure 12:
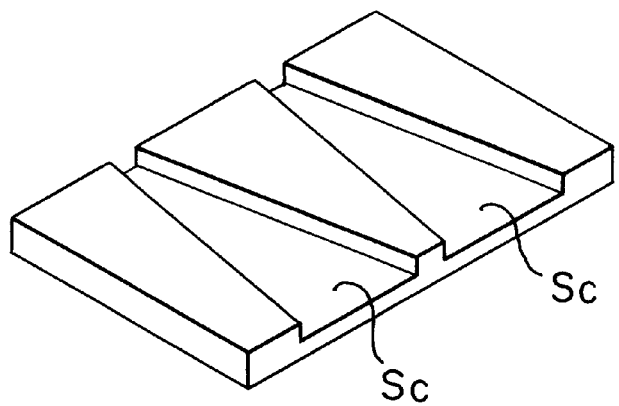
FIG. 12 is a perspective view of a modification of the sixth preferred embodiment of a measuring chip for an optical analyzer according to the present invention.

FIG. 11 shows the sixth preferred embodiment of a measuring chip for an optical analyzer according to the present invention. Unlike the above described measuring chips having the sample solution chamber formed by stacking thin films, a measuring chip A5 in this preferred embodiment has a plastic block 13a, which has two grooves formed in the bottom thereof and which is stacked on a translucent or transparent substrate 1 to form two sample solution chambers Sa, Sb. The grooves for the sample solution chambers Sa, Sb may be formed by the injection molding using a metal mold, or by cutting a formed square block by means of a milling machine. The shapes of the sample solution chambers may be optionally selected. As shown in FIG. 12 (which shows the reverse surface of a plastic block), the inlet and outlet of each of sample solution chambers Sc may have different cross-sectional areas. It is not required to integrally form the two sample solution chambers as shown in FIG. 11; only one sample solution chamber may be formed. In the measuring chip A6 with this construction, there are advantages in that the efficiency of the assembling process can be improved by decreasing the number of parts, and the yield can be improved. The optimum plastic material is selected in accordance with the optical analyzing means and object. In a case where the measuring chip is used for all optical analyzer utilizing the surface plasmon resonance, the measuring chip may be made of a general plastic, and it is preferably made of a transparent material having a good adhesive property. Because it is easy to identify the quantity of the sample solution in the sample solution chamber and to put the block on the substrate during assembly.

Figure 13:
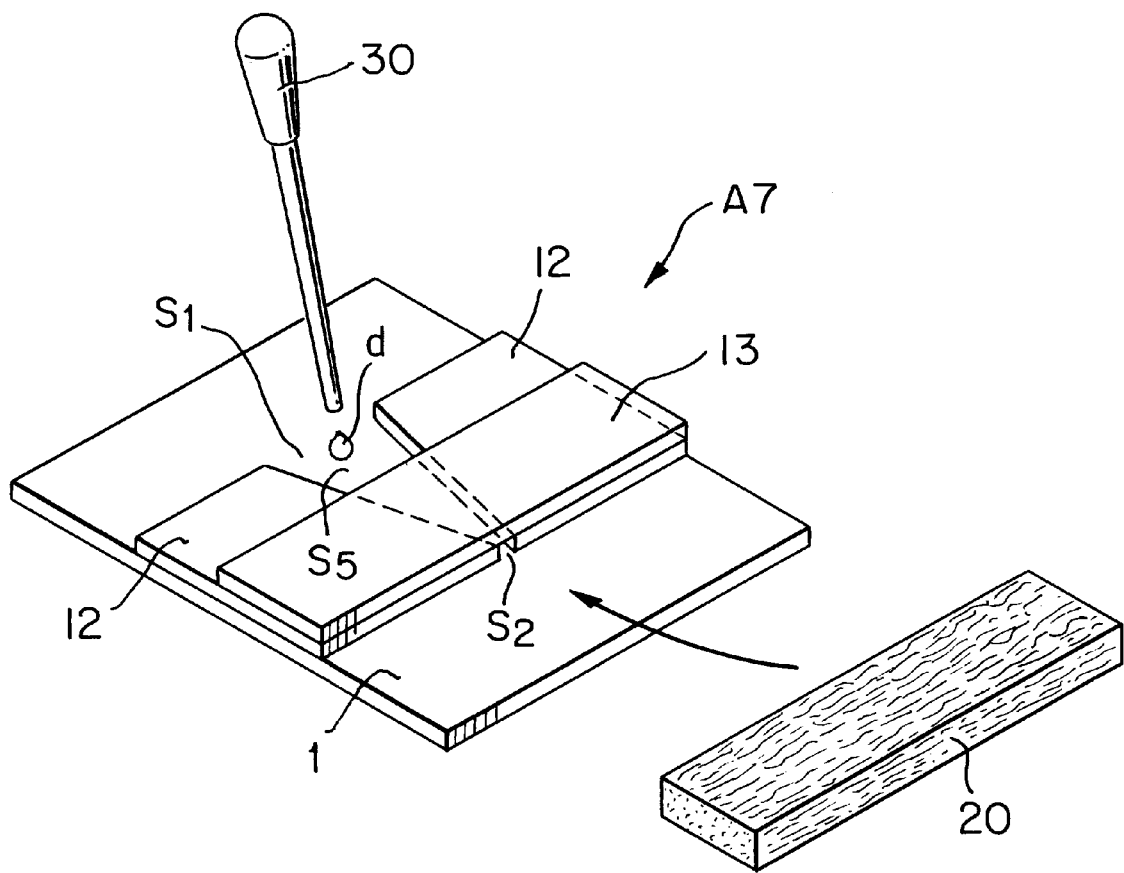
FIG. 13 is a perspective view of the seventh preferred embodiment of a measuring chip for an optical analyzer according to the present invention.

FIG. 13 shows the seventh preferred embodiment of a measuring chip for an optical analyzer according to the present invention. In this preferred embodiment, the right and left side walls of a sample solution chamber (space) S are inclined with respect to the flowing direction of the sample solution so that the cross-sectional area of the outlet $S_2$ of the sample solution chamber (space) S is smaller than that of the inlet $S_1$ thereof, and the width of a top board 13 is less than those of side plates 12 so that the inlet of the sample solution chamber S has an upward open portion $S_5$. At these points, a measuring chip A7 in this preferred embodiment is different from the measuring chip A1. In this case, there are advantages in that all the sample solution can be surely discharged from the sample solution chamber by means of the absorbing pad 20 and that the sample solution can be easily supplied to the sample solution chamber S.

Figure 14:
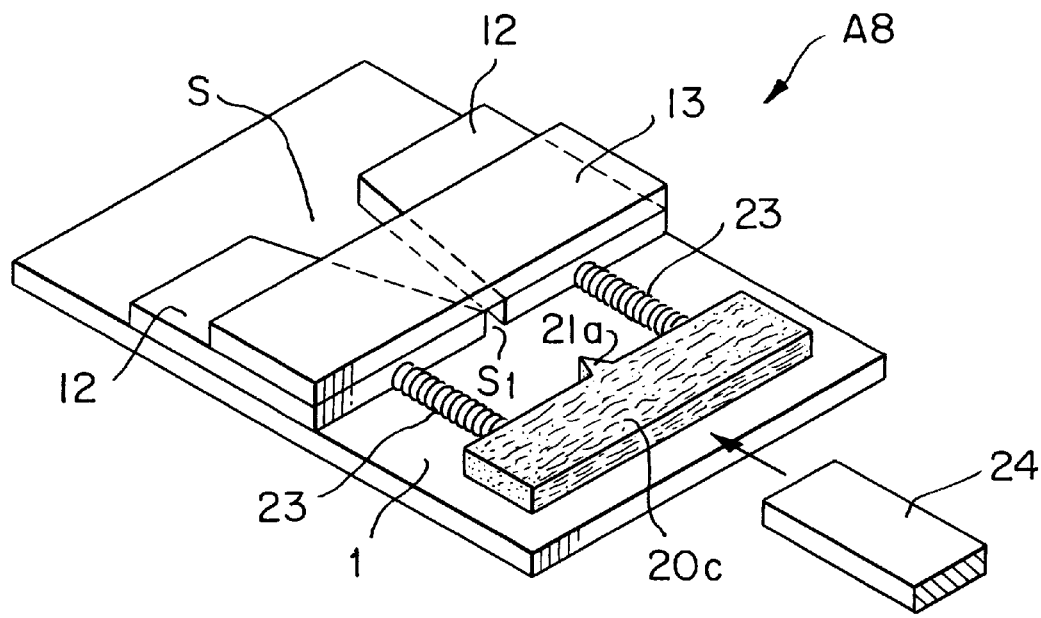
FIG. 14 is a perspective view of the eighth preferred embodiment of a measuring chip for an optical analyzer according to the present invention.

FIG. 14 shown the eighth preferred embodiment of a measuring chip for an optical analyzer according to the present invention. In this preferred embodiment, an absorbing pad 20c is sidably arranged on a translucent, or transparent substrate 1. At this point, a measuring chip A8 in this preferred embodiment is different from the measuring chips described referring to FIGS. 1 through 13. In this measuring chip A8, the absorbing pad 20c is mounted on the side of the outlet $S_2$ of a sample solution chamber S so as to be slidable between a position, at which the absorbing pad 20c contacts the outlet $S_2$ and a position, at which the absorbing pad 20c is apart from the outlet $S_2$ (the position shown in FIG. 14), by means of coil springs 23. When the absorbing pad 20c is pressed toward the outlet $S_2$ by means of, e.g., an operating rod 24, a projection 21a formed at the tip of the absorbing pad 20c is inserted into the outlet $S_2$ to start to absorb the solution. After a predetermined period of time, when the pressing of the operating rod 24 is released, the absorbing pad 20c, which has absorbed the solution, returns to the shown position apart from the outlet by the spring force of the coil springs 23. With this construction, there is an advantage in that the supply and discharge of the sample solution can be accurately controlled without the need of any complicated supplying systems. While the measuring chip A7 shown in FIG. 13 has been used in FIG. 14, the shape of the measuring chip should not be limited thereto, but other shapes may be optionally used.

Figure 15:
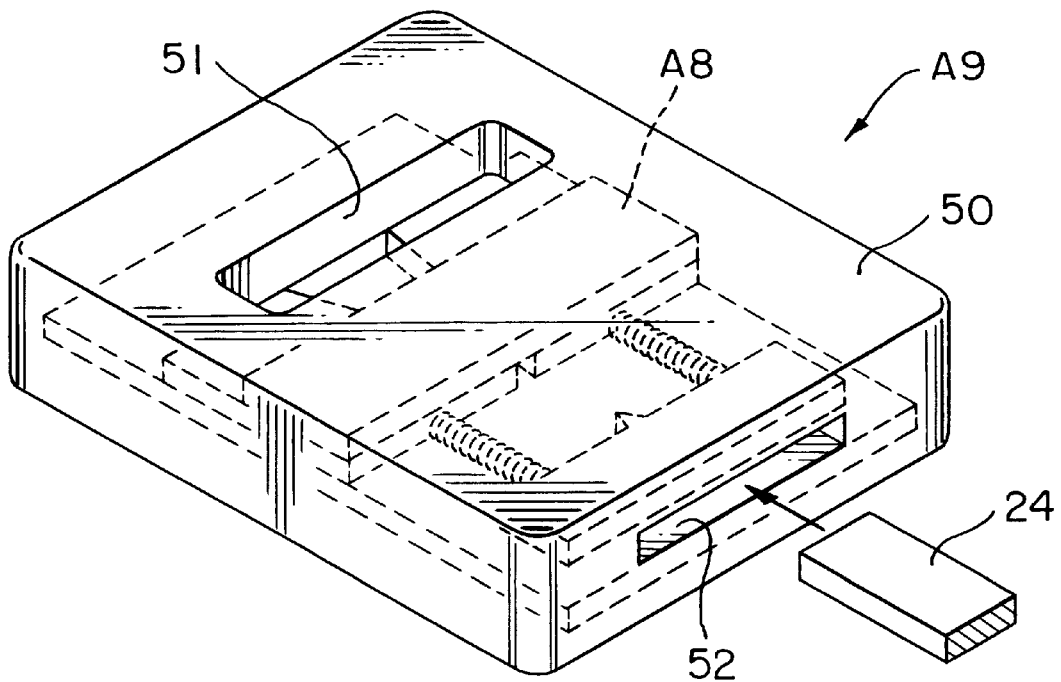
FIG. 15 is a perspective view of the ninth preferred embodiment of a measuring chip for an optical analyzer according to the present invention.

FIG. 15 shows the ninth preferred embodiment of a measuring chip for an optical analyzer according to the present invention. In this preferred embodiment, a measuring chip A9 is housed in a casing 50 having a sample solution supply port 51. At this point, the measuring chip A9 is different from the measuring chips described referring to FIGS. 1 through 14. In this measuring chip A9, the sample solution supply port 51 is formed above the inlet $S_1$ of a sample solution chamber, so that the operator can easily supply a required sample solution or the like through the sample solution supply port 51 by means of a pipette 30. In FIG. 15, the measuring chip A8 shown in FIG. 14 is used, so that an opening 52 for inserting the tip of the operating rod 24 is formed in a side of the casing 50. However, the measuring chip should not be limited thereto, but other measuring chips may be optionally used when the operating rod 24 or the like is not used, the opening 52 is not required. In this measuring chip A9, there are advantages in that the waste solution can be treated in the measuring chip and discharged without contacting the operator's hand.

FIGS. 16(a) and 16(b) show embodiments of a sample solution chamber of a measuring chip for an optical analyzer according to the present invention, which are viewed from the bottom. In FIG. 16(a), a pair of side plates 12A having side walls 12d, which are inclined with respect to the flowing direction of the sample solution, are formed on a substrate 13A having an inclined upper surface 13a. In this embodiment, since both of the side walls 12d and the upper surface (top surface) 13a of the sample solution chamber are inclined, there are advantages in that the cross-sectional area of the sample solution chamber S can be rapidly changed in comparison with those of the sample solution chambers shown in FIGS. 6, 7, 12 and 13 and it is difficult to run out of the solution. In FIG. 16(b), a sample solution chamber S having the same shape as that of the sample solution chamber shown in FIG. 16(a) is integrally formed by injection-molding a resin by means of a metal mold. In this case, there are advantages in that the efficiency of the assembly process and the yield can be improved by decreasing the number of parts. The light and left side walls of the sample solution chamber may be parallel to each other and only at least one of the upper surface and the upper and lower surfaces may be inclined with respect to the measurement reference surface to change the cross-sectional area of the sample solution chamber, although it is not shown. In addition, the measuring chip for the optical analyzer is formed by suitably arranging the sample solution chamber shown in FIG. 16a or (16b on a translucent or transparent substrate 1 similar to that shown in FIG. 12. In this case, openings may selectively serve as either of inlet and outlet. A plurality of sample solution chambers having the same shape as that of the above sample solution chamber may be formed in parallel.

While the preferred embodiments of a measuring chip for an optical analyzer utilizing the surface plasmon resonance according to the present invention have been described, the present invention should not be limited thereto, but the invention can be embodied in various ways without departing from the principle of the invention. For example, when an analysis using, as a variable, a transmitted light passing through the sample solution d not a reflected light, such as an optical analysis for detecting a color reaction of oxygen, is carried out, the metal thin film 2 and the immobilizing film 3 are not required, and the top board 13 is made of a translucent or transparent material. In addition, when an ultraviolet region is detected, the material of a portion of the measuring chip contacting the sample solution is preferably quartz glass, although it is not required to change the material of the measuring chip when a visible light region is detected.

As described above, if a measuring chip for an optical analyzer according to the present invention is used, a required optical analysis can be carried out by dropping only a droplet or a few droplet of sample solution. Therefore, the pretreatment for analysis as well as the after-treatment can be simplified, and the quantity of wasteful sample solution can be decreased, so that the optical analysis operation can be carried out at low costs. In addition, it is expected that errors depending on the operator's level of skill can be decreased, so that anyone can accurately and simply carry out measurement.

While the present invention has been disclosed in terms of the preferred embodiment in order to facilitate better understanding thereof, it should be appreciated that the invention can be embodied in various ways without departing from the principle of the invention. Therefore, the invention should be understood to include all possible embodiments and modification to the shown embodiments which can be embodied without departing from the principle of the invention as set forth in the appended claims.

What is claimed is:

1. A measuring chip for an optical analyzer, said chip comprising:

a translucent or transparent substrate; and a sample solution chamber having an inlet for introducing a sample solution to be analyzed and an outlet for discharging the analyzed sample solution, said sample solution chamber being formed on a surface of said translucent or transparent substrate in a manner so that the interior of said sample solution chamber between said inlet and a vicinity of said outlet is filled with said sample solution by capillary action, both said inlet and said outlet being opened to the outside of said sample solution chamber so that said sample solution chamber is formed as an open system for said sample solution.

2. A measuring chip for an optical analyzer as set forth in claim 1, which further comprises an immobilizing film for immobilizing a physiologically active substance, said immobilizing film being formed on at least a part of the surface of said translucent or transparent substrate, at least a part of said immobilizing film facing said sample solution chamber.

3. A measuring chip for an optical analyzer as set forth in claim 1, which further comprises a metal thin film formed on at least a part of the surface of said translucent or transparent substrate, and an immobilizing film, formed on said metal thin film, for immobilizing a physiologically active substance, at least a part of said immobilizing film facing said sample solution chamber.

4. A measuring chip for an optical analyzer as set forth in claim 1, wherein said outlet of said sample solution chamber has a greater cross-sectional area than that of said inlet thereof.

5. A measuring chip for an optical analyzer as set forth in claim 1, wherein said outlet of said sample solution chamber has a smaller cross-sectional area than that of said inlet thereof.

6. A measuring chip for an optional analyzer as set forth in claim 1, wherein said sample solution chamber has a lower surface positioned at an upper side of said translucent or transparent substrate and an upper surface positioned above said lower surface and one or both of said upper and lower surfaces of said sample solution chamber are inclined with respect to a measurement reference surface located downside of said translucent or transparent substrate.

7. A measuring chip for an optical analyzer as set forth in claim 1, which further comprises absorbing pad means for absorbing and discharging said sample solution filled in said analyzed sample solution chamber.

8. A measuring chip for an optical analyzer as set, forth in claim 7, wherein said absorbing pad means comprises a plurality of absorbing pads having different rates of absorption.

9. A measuring chip for an optical analyzer as set forth in claim 7, wherein said absorbing pad means is arranged on said translucent or transparent substrate so as to be slidable between a first position, at which said absorbing pad means contacts said outlet, and a second position, at which said absorbing pad means is apart from said outlet.

10. A measuring chip for an optical analyzer as set forth in claim 9, which further comprising means for sliding said absorbing pad means.

11. A measuring chip for an optical analyzer as set forth in claim 1, which further comprises a carrying holder for holding a peripheral portion of said translucent or transparent substrate.

12. A measuring chip for an optical analyzer as set, forth in claim 1, wherein said measuring chip is housed in a casing having a sample solution supply port.

13. A measuring chip for an optical analyzer as set, forth in claim 1, wherein said sample solution chamber has a reference region and a sample region.

14. A measuring chip for an optional analyzer as set forth in claim 1, wherein said sample solution chamber has a sidewall positioned on an upper lateral side of said translucent or transparent substrate and a top board positioned above said translucent or transparent substrate and said sample solution chamber is formed by stacking a member serving as said side wall and said member serving as said top board.

15. A measuring chip for an optional analyzer as set forth in claim 1, wherein said translucent or transparent substrate is made of a plastic block and said sample solution chamber is formed by removing a bottom from said plastic block.

16. A measuring chip for an optical analyzer, said chip comprising:

a translucent or transparent substrate; and a plurality of sample solution chambers, each of said sample solution chambers having an inlet for introducing a sample solution to be analyzed and an outlet for discharging the analyzed sample solution, said sample solution chambers being formed on a surface of said translucent or transparent substrate in a manner so that the interior of each of said sample solution chambers between said inlet and a vicinity of said outlet is filled with said sample solution by capillary action, both said inlet and said outlet being opened to the outside of said sample solution chamber so that said sample solution chamber is formed as an open system for said sample solution.

17. A measuring chip for an optical analyzer as set forth in claim 16, which further comprises an immobilizing film for immobilizing a physiologically active substance, said immobilizing film being formed on at least a part of the surface of said translucent or transparent substrate, at least a part of said immobilizing film facing said sample solution chambers.

18. A measuring chip for an optical analyzer as set forth in claim 16, which further comprises a metal thin film formed on at least a part of the surface of said translucent or transparent substrate, and an immobilizing film, formed on said metal thin film, for immobilizing a physiologically active substance, at least a part of said immobilizing film facing said sample solution chambers.

19. A measuring chip for an optical analyzer as set, forth in claim 16, wherein said outlet of at least one of said sample solution chambers has a greater cross-sectional area than that of said inlet thereof.

20. A measuring chip for an optical analyzer as set forth in claim 16, wherein said outlet of at least one of said sample solution chambers has a smaller cross-sectional area than that of said inlet thereof.

21. A measuring chip for an optional analyzer as set forth in claim 16, wherein said sample solution chamber has a lower surface positioned at an upper side of said translucent or transparent substrate and an upper surface positioned above said lower surface and one or both of said upper and lower surfaces of said sample solution chamber are inclined with respect to a measurement reference surface located downside of said translucent or transparent substrate.

22. A measuring chip for an optical analyzer as set forth in claim 16, which further comprises absorbing pad means for absorbing and discharging said sample solution filled in said sample solution chambers.

23. A measuring chip for an optical analyzer as set forth in claim 22, wherein said absorbing pad means comprises a plurality of absorbing pads having different rates of absorption.

24. A measuring chip for an optical analyzer as set forth in claim 22, wherein said absorbing pad means is arranged on said translucent or transparent substrate so as to be slidable between a first position, at which said absorbing pad means contacts said outlet, and a second position, at which said absorbing pad means is apart from said outlet.

25. A measuring chip for an optical analyzer as set forth in claim 24, which further comprising means for sliding said absorbing pad means.

26. A measuring chip for an optical analyzer as set forth in claims 16, which further comprises a carrying holder for holding a peripheral portion of said translucent or transparent substrate.

27. A measuring chip for an optical analyzer as set forth in claim 16, wherein said measuring chip is housed in a casing having a sample solution supply port.

28. A measuring chip for an optical analyzer as set forth in claim 16, wherein at least one of said sample solution chambers has a reference region and a sample region.

29. A measuring chip for an optical analyzer as set forth in claim 16, wherein any one of said sample solution chambers is a sample solution chamber for reference.

30. A measuring chip for an optional analyzer as set forth in claim 16, wherein said sample solution chamber has a sidewall positioned on an upper lateral side of said translucent or transparent substrate and a top board positioned above said translucent or transparent substrate and said sample solution chamber is formed by stacking a member serving as said side wall and said member serving as said top board.

31. A measuring chip for an optional analyzer as set forth in claim 16, wherein said translucent or transparent substrate is made of a plastic block and said sample solution chamber is formed by removing a bottom from said plastic block.

* * * * *